(12) United States Patent
Vogel et al.

(10) Patent No.: US 7,928,251 B2
(45) Date of Patent: Apr. 19, 2011

(54) PROCESS FOR PREPARING TETRAMETHYL GLYCOLIDE

(75) Inventors: Bernd Vogel, Wiesbaden (DE); Alexander May, Darmstadt (DE); Hermann Siegert, Seeheim-Jugenheim (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 12/443,784

(22) PCT Filed: Aug. 30, 2007

(86) PCT No.: PCT/EP2007/059038
§ 371 (c)(1), (2), (4) Date: Mar. 31, 2009

(87) PCT Pub. No.: WO2008/061821
PCT Pub. Date: May 29, 2008

(65) Prior Publication Data
US 2010/0010276 A1    Jan. 14, 2010

(30) Foreign Application Priority Data

Nov. 22, 2006  (DE) .......................... 10 2006 055 427

(51) Int. Cl.
*C07D 319/12* (2006.01)
(52) U.S. Cl. ....................................... 549/274; 549/379
(58) Field of Classification Search .................. 549/274, 549/379
See application file for complete search history.

(56) References Cited

U.S. PATENT DOCUMENTS

| | | | |
|---|---|---|---|
| 5,225,594 A | 7/1993 | Shima et al. | |
| 5,420,304 A * | 5/1995 | Verser et al. | 549/274 |
| 6,743,407 B2 | 6/2004 | Schaefer et al. | |
| 6,977,310 B2 | 12/2005 | Ackermann et al. | |
| 6,979,432 B2 | 12/2005 | Schaefer et al. | |
| 7,288,402 B2 | 10/2007 | Osswald et al. | |
| 7,491,521 B2 | 2/2009 | Osswald et al. | |
| 2006/0211880 A1 | 9/2006 | Ackerman et al. | |
| 2007/0173664 A1 | 7/2007 | Krill et al. | |
| 2008/0194862 A1 | 8/2008 | Ackermann et al. | |
| 2008/0194875 A1 | 8/2008 | Ackermann et al. | |
| 2008/0248538 A1 | 10/2008 | Osswald et al. | |
| 2008/0269431 A1 | 10/2008 | Sarcinelli et al. | |
| 2009/0118533 A1 | 5/2009 | Broell et al. | |

FOREIGN PATENT DOCUMENTS

| | | |
|---|---|---|
| EP | 0 487 853 | 6/1992 |
| JP | 10059958 * | 3/1998 |
| WO | 95 09142 | 4/1995 |
| WO | 2005 077878 | 8/2005 |

OTHER PUBLICATIONS

Golomb, A. et al., "Studies In Pyrolysis. Part XVII. The Acyl Derivatives and Lactides of Some α-Hydroxy-Acid", J. Chem. Soc., pp. 838-847 (1962) XP009092793.
U.S. Appl. No. 12/300,189, filed Nov. 10, 2008, Broell et al.
U.S. Appl. No. 12/299,217, filed Oct. 31, 2008, Broell et al.
U.S. Appl. No. 12/307,773, filed Jan. 7, 2009, Ackermann et al.
U.S. Appl. No. 12/441,145, filed Mar. 13, 2009, May et al.
U.S. Appl. No. 12/515,036, filed May 15, 2009, May et al.
U.S. Appl. No. 12/442,415, filed Mar. 23, 2009, Vogel et al.
U.S. Appl. No. 12/303,161, filed Dec. 2, 2008, Marx et al.

* cited by examiner

*Primary Examiner* — Elvis O Price
(74) *Attorney, Agent, or Firm* — Oblon, Spivak, McClelland, Maier & Neustadt, L.L.P.

(57) ABSTRACT

The present invention relates to a process for preparing tetramethylglycolide by heating a composition which comprises at least 50% by weight of 2-hydroxy-isobutyric acid and/or tetramethylglycolide to a temperature of at least 100° C.

24 Claims, 2 Drawing Sheets

PROCESS FOR PREPARING TETRAMETHYL GLYCOLIDE

The present invention relates to processes for preparing tetramethylglycolide comprising the reaction of 2-hydroxyisobutyric acid.

Cyclic esters have been used for some time, especially for the preparation of biodegradable polymers, the preparation of these esters from α-hydroxycarboxylic acids being long-established prior art. For example, the publication DE 26 78 26 describes a process for preparing a lactide in which lactic acid is heated slowly to a temperature of 200° C. and the lactide formed is distilled off, advantageously under reduced pressure. In this process, oligomers and polymers of lactic acid in particular are formed. Accordingly, the process is afflicted with many disadvantages. These include in particular the low purity of the resulting products and the low yield.

In addition, processes for preparing cyclic esters are known, in which a polyester, especially polylactides, are depolymerized to form cyclic esters. Such processes form the subject-matter, for example, of the publication DE-A-37 08 915, further prior art being cited in the introductory part of this document. A disadvantage of these processes is in particular that polymers first have to be prepared and purified. These processes are therefore relatively expensive owing to the starting materials used.

In addition, the document WO 95/09142 describes processes for preparing cyclic esters in which an aqueous phase of an α-hydroxycarboxylic acid is initially prepared. The α-hydroxycarboxylic acid is withdrawn from the aqueous phase by an extraction with an organic solvent. The organic phase is then admixed with a further solvent which has a higher boiling point than the extractant. The extractant is removed in a further step. Subsequently, the α-hydroxycarboxylic acid present in this reaction mixture is converted to the cyclic ester, the proportion of oligomers and polymers being kept at less than 20% by weight. Thereafter, the resulting cyclic ester can be removed from by-products by extraction or crystallization. This process is very complicated, since many steps are necessary to purify the resulting products. In addition, the content of oligomers and/or polymers has to be kept at a low level. However, this includes the fact that the concentration of reactant has to be kept relatively low. Therefore, very high amounts of solvents have to be removed.

Moreover, the document EP-A-0 834 511 describes the preparation and purification of cyclic esters. The cyclic esters are obtained here either by depolymerization of polymers or by cyclization of α-hydroxycarboxylic acids in solution. The crucial step is the reaction of the resulting reaction product with ortho esters in order to reduce the content of water and acid in the product. This process leads to a good product. However, the ortho esters to be used are relatively expensive, such that the overall process can be improved.

Even though the processes described in the documents cited above can already be used for the preparation of cyclic esters, there is a permanent need to improve these processes further in order to lower the preparation costs and to improve the yields.

In view of the prior art, it is thus an object of the present invention to provide processes for preparing cyclic esters which can be performed in a particularly simple and inexpensive manner and with high yield. A particular problem consisted in particular in providing a process which can be used flexibly to prepare different products in order thus to ensure high utilization of the production plants used.

This object and further objects which are not stated explicitly but which are derivable or discernible immediately from the connections discussed herein by way of introduction are achieved by a process having all features of claim 1. Appropriate modifications of the processes according to the invention are protected in subclaims.

Figure 1:
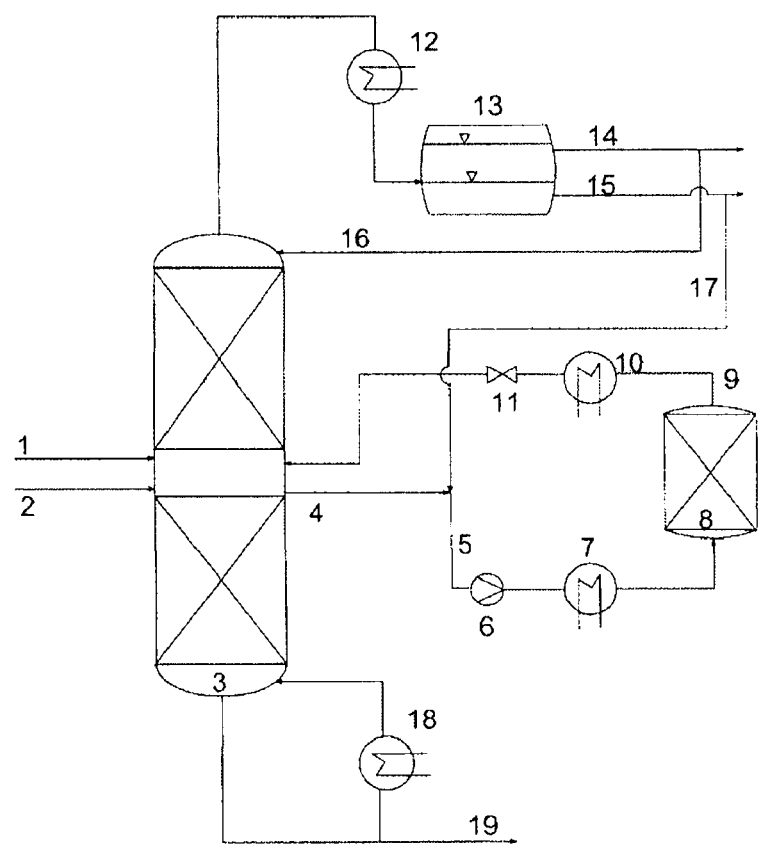
FIG. 1 is a schematic of one embodiment of a still that is described herein.

The present invention accordingly provides a process for preparing tetramethylglycolide, characterized in that a composition which comprises at least 50% by weight of 2-hydroxyisobutyric acid and/or tetramethyl-glycolide is heated to a temperature of at least 100° C. The process can be performed in a particularly simple and inexpensive manner and with high yield.

At the same time, the processes according to the invention can achieve a series of further advantages. One is that the process is particularly flexible. In this context, the process can be configured such that, in addition to tetramethylglycolide, further products, for example alkyl methacrylate and/or methacrylic acid, can be obtained. In addition, the process according to the invention can be performed at high speed, low energy input and low yield losses.

The compound tetramethylglycolide (3,3,6,6-tetramethyl-1,4-dioxane-2,5-dione) is known per se from the prior art and can be obtained by dimerizing 2-hydroxyisobutyric acid, as described, for example, in EP-A-0 834 511.

According to the invention, tetramethylglycolide is obtained by the reaction of a composition which comprises at least 50% by weight of 2-hydroxyisobutyric acid and/or tetramethylglycolide. The composition preferably comprises at least 70% by weight and most preferably at least 90% by weight of 2-hydroxy-isobutyric acid and/or tetramethylglycolide. The expression "hydroxyisobutyric acid and/or tetramethyl-glycolide" clarifies that the composition, as well as the reactant and the product, comprises only relatively small proportions of solvents or other substances. However, solvents may be present in the reaction mixture. Solvents having a low boiling point may be removed via the top in the case of a reaction in a still. These solvents may serve in particular to keep the addition temperature of the reactant mixture low. This may be appropriate especially in the case of continuous processes. In addition, this allows the temperature at the start of the reaction to be kept low, so that particularly low proportions of undesired by-products are formed. Solvents with high boiling points remain in the product in many cases in the case of a reaction in a still. In many cases, these solvents lower the solidification temperature, such that the product stream can be discharged from the still at relatively low temperatures.

The suitable solvents include, for example, alcohols, ketones, aldehydes, esters, ethers, carboxylic acids, hydrocarbons and mixtures of these solvents with one another and with further solvents.

The hydrocarbon solvents include aliphatic, alicyclic and aromatic hydrocarbons. These hydrocarbons include pentane, hexane, especially n-hexane and 3-methyl-pentane, heptane, especially n-heptane and 3-methyl-hexane, octane, cyclopentane, cyclohexane, benzene, toluene, xylene, ethylbenzene.

In addition, the suitable solvents include carboxylic acids and carboxylic esters. These include in particular acetic acid, ethyl acetate, α-hydroxy-carboxylic acids, especially 2-hydroxyisobutyric acid and methyl 2-hydroxyisobutyrate.

The ketones usable as solvents include, for example, acetone, methyl ethyl ketone, diethyl ketone, methyl propyl ketone, methyl isopropyl ketone, methyl butyl ketone, methyl 1-methylpropyl ketone, methyl 2-methyl-propyl ketone, ethyl propyl ketone and other ketones having 2 or more carbon atoms in each case, preferably 4 to 12 and more preferably 4 to 9 carbon atoms.

The aldehydes usable as solvents include, for example, acetaldehyde, propionaldehyde, butyraldehyde, valeraldehyde, benzaldehyde and other aldehydes having 2 or more carbon atoms in each case, preferably 4 to 12 and more preferably 4 to 9 carbon atoms.

The ethers usable as solvents include diethyl ether, di-n-propyl ether, diisopropyl ether, di-n-butyl ether, diisobutyl ether and other ethers having in each case 2 or more carbon atoms, preferably 4 to 12 and more preferably 4 to 9 carbon atoms.

Alcohols may be used with particular preference as solvents. The preferred alcohols include alcohols having at least one carbon atom in each case, preferably 2 to 12 and more preferably 4 to 9 carbon atoms. The alcohols may have a linear, branched or cyclic structure. In addition, the alcohols may comprise aromatic groups or substituents, for example halogen atoms. The preferred alcohols include in particular methanol, ethanol, n-propanol, isopropanol, n-butanol, 1-methyl-propanol, 2-methylpropanol, tert-butanol, n-pentanol, 1-methylbutanol, 2-methylbutanol, 3-methylbutanol, 2,2-dimethylpropanol, n-hexanol, 1-methylpentanol, 2-methylpentanol, 3-methylpentanol, 4-methylpentanol, 1,1-dimethylbutanol, 2,2-dimethylbutanol, 3,3-dimethyl-butanol, 1,2-dimethylbutanol, n-heptanol, 1-methyl-hexanol, 2-methylhexanol, 3-methylhexanol, 4-methyl-hexanol, 1,2-dimethylpentanol, 1,3-dimethylpentanol, 1,1-dimethylpentanol, 1,1,2,2-tetramethylpropanol, benzyl alcohol, n-octanol, 2-ethylhexanol, n-nonanol, 1-methyloctanol, 2-methyloctanol, n-decanol, n-undecanol, 1-methyldecanol, 2-methyldecanol, n-dodecanol, 2,4-diethyloctanol, cyclopentanol, cyclohexanol, 4-tert-butylcyclohexanol, cycloheptanol, cyclododecanol, 2-(dimethylamino)ethanol, 3-(dimethyl-amino)propanol, 4-(dimethylamino)butanol, 5-(dimethyl-amino)pentanol, 6-(dimethylamino)hexanol, 8-(dimethyl-amino)octanol, 10-(dimethylamino)decanol, 12-(dimethyl-amino)dodecanol, 2-(diethylamino)ethanol, 3-(diethyl-amino)propanol, 4-(diethylamino)butanol, 5-(diethyl-amino)pentanol, 6-(diethylamino)hexanol, 8-(diethyl-amino)octanol, 10-(diethylamino)decanol, 12-(diethyl-amino)dodecanol, 2-(di(isopropyl)amino)ethanol, 3-(di(isopropyl)amino)propanol, 4-(di(isopropyl)amino)-butanol, 5-(di(isopropyl)amino)pentanol, 6-(di(iso-propyl)amino)hexanol, 8-(di(isopropyl)amino)octanol, 10-(di(isopropyl)amino)decanol, 12-(di(isopropyl)-amino)dodecanol, 2-(dibutylamino)ethanol, 3-(dibutyl-amino)propanol, 4-(dibutylamino)butanol, 5-(dibutyl-amino)pentanol, 6-(dibutylamino)hexanol, 8-(dibutyl-amino)octanol, 10-(dibutylamino)decanol, 12-(dibutyl-amino)dodecanol, 2-(dihexylamino)ethanol, 3-(dihexyl-amino)propanol, 4-(dihexylamino)butanol, 5-(dihexyl-amino)pentanol, 6-(dihexylamino)hexanol, 8-(dihexyl-amino)octanol, 10-(dihexylamino)decanol, 12-(dihexyl-amino)dodecanol, 2-(methylethylamino)ethyl, 2-(methyl-propylamino)ethanol, 2-(methylisopropylamino)ethanol, 2-(methylbutylamino)ethanol, 2-(methylhexylamino)-ethanol, 2-(methyloctylamino)ethanol, 2-(ethylpropyl-amino)ethanol, 2-(ethylisopropylamino)ethanol, 2-(ethylbutylamino)ethanol, 2-(ethylhexylamino)ethanol, 2-(ethyloctylamino)ethanol, 3-(methylethylamino)propanol, 3-(methylpropylamino)propanol, 3-(methylisopropylamino)propanol, 3-(methylbutylamino)propanol, 3-(methylhexylamino)propanol, 3-(methyloctylamino)propanol, 3-(ethylpropylamino)-propanol, 3-(ethylisopropylamino)propanol, 3-(ethyl-butylamino)propanol, 3-(ethylhexylamino)propanol, 3-(ethyloctylamino)propanol, 4-(methylethylamino)-butanol, 4-(methylpropylamino)butanol, 4-(methyliso-propylamino)butanol, 4-(methylbutylamino)butanol, 4-(methylhexylamino)butanol, 4-(methyloctylamino)-butanol, 4-(ethylpropylamino)butanol, 4-(ethyliso-propylamino)butanol, 4-(ethylbutylamino)butanol, 4-(ethylhexylamino)butanol, 4-(ethyloctylamino)butanol, 2-(N-piperidinyl)ethanol, 3-(N-piperidinyl)propanol, 4-(N-piperidinyl)butanol, 5-(N-piperidinyl)pentanol, 6-(N-piperidinyl)hexanol, 8-(N-piperidinyl)octanol, 10-(N-piperidinyl)decanol, 12-(N-piperidinyl)dodecanol, 2-(N-pyrrolidinyl)ethanol, 3-(N-pyrrolidinyl)propanol, 4-(N-pyrrolidinyl)butanol, 5-(N-pyrrolidinyl)pentanol, 6-(N-pyrrolidinyl)hexanol, 8-(N-pyrrolidinyl)octanol, 10-(N-pyrrolidinyl)decanol, 12-(N-pyrrolidinyl)-dodecanol, 2-(N-morpholino)ethanol, 3-(N-morpholino)-propanol, 4-(N-morpholino)butanol, 5-(N-morpholino)-pentanol, 6-(N-morpholino)hexanol, 8-(N-morpholino)-octanol, 10-(N-morpholino)decanol, 12-(N-morpholino)-dodecanol, 2-(N'-methyl-N-piperazinyl)ethanol, 3-(N'-methyl-N-piperazinyl)propanol, 4-(N'-methyl-N-piperazinyl)butanol, 5-(N'-methyl-N-piperazinyl)-pentanol, 6-(N'-methyl-N-piperazinyl)hexanol, 8-(N'-methyl-N-piperazinyl)octanol, 10-(N'-methyl-N-piperazinyl)decanol, 12-(N'-methyl-N-piperazinyl)-dodecanol, 2-(N'-ethyl-N-piperazinyl)ethanol, 3-(N'-ethyl-N-piperazinyl)propanol, 4-(N'-ethyl-N-piperazinyl)butanol, 5-(N'-ethyl-N-piperazinyl)-pentanol, 6-(N'-ethyl-N-piperazinyl)hexanol, 8-(N'-ethyl-N-piperazinyl)octanol, 10-(N'-ethyl-N-piperazinyl)decanol, 12-(N'-ethyl-N-piperazinyl)dodecanol, 2-(N'-isopropyl-N-piperazinyl)-ethanol, 3-(N'-isopropyl-N-piperazinyl)propanol, 4-(N'-isopropyl-N-piperazinyl)butanol, 5-(N'-isopropyl-N-piperazinyl)pentanol, 6-(N'-isopropyl-N-piperazinyl)-hexanol, 8-(N'-isopropyl-N-piperazinyl)octanol, 10-(N'-isopropyl-N-piperazinyl)decanol, 12-(N'-isopropyl-N-piperazinyl)dodecanol, 3-oxabutanol, 3-oxapentanol, 2,2-dimethyl-4-oxapentanol, 3,6-dioxaheptanol, 3,6-dioxaoctanol, 3,6,9-trioxadecanol, 3,6,9-trioxaundecanol, 4-oxapentanol, 4-oxahexanol, 4-oxaheptanol, 4,8-dioxanonanol, 4,8-dioxadecanol, 4,8-dioxaundecanol, 5-oxahexanol or 5,10-dioxaundecanol.

In addition, ethoxylated and/or propoxylated alcohols and mixed ethoxylated/propoxylated alcohols may be used as solvents, in particular $R^5$—(O—$CH_2$—$CH_2$)$_x$—OH or
$R^5$—(O—CH($CH_3$)—$CH_2$)$_x$—OH, and/or $R^5$—(O—$CH_2$—CH($CH_3$))$_x$—OH, in which
$R^5$ is $C_1$ to $C_{20}$-alkyl and
x is an integer from 10 to 20,
or ethoxylated and/or propoxylated amino alcohols, for example
$R^6_2$N(—$CH_2$—$CH_2$—O)$_y$—H or $R^6_2$N(—CH($CH_3$)—$CH_2$—O)$_y$—H and/or
$R^6_2$N(—$CH_2$CH($CH_3$)—O)$_y$—H,
in which y is an integer from 1 to 4. $R^6$ is an alkyl group having 1-6 carbon atoms, where the nitrogen with the substituents $R^6$ may also form a five- to seven-membered ring. The ring may optionally also be substituted by one or more short-chain alkyl groups, for example methyl, ethyl or propyl.

According to the invention, the composition comprising 2-hydroxyisobutyric acid is heated to a temperature of at least 100° C., preferably at least 150° C. and more preferably at least 170° C. The upper temperature limit arises in particular from the boiling point of the composition if the reaction is performed in the liquid phase.

The reaction is effected preferably in the liquid phase, in which case a catalyst, especially an acidic catalyst, can be added. In this case, both homogeneous and heterogeneous catalysts can be used. Particularly suitable catalysts are in particular inorganic acids, for example sulphuric acid or hydrochloric acid, and organic acids, for example sulphonic acids, especially p-toluenesulphonic acid, and acidic cation exchangers. In a particularly preferred aspect, the reaction is effected autocatalytically.

The reaction can be effected at reduced or elevated pressure depending on the reaction temperature. Preference is given to performing this reaction at a pressure in the range of 0.001-5 bar, in particular 0.005 to 1 bar and more preferably 0.1 to 0.4 bar.

The reaction can be performed batchwise or continuously, preference being given to continuous processes. In a particular aspect of the present invention, the preparation of tetramethylglycolide can be effected in a still. Distillation systems suitable for this purpose are common knowledge and are frequently used for separation. The use of a still to perform the inventive reaction enables in particular the removal of water formed from the reaction mixture by distillation. This way of influencing the reaction equilibrium is particularly economical. However, water formed can likewise be removed by other processes.

The still can be prepared from any material suitable for this purpose. This includes stainless steel and inert materials.

The reaction time of the inventive reaction depends upon the reaction temperature, and this parameter may be within wide ranges. The reaction time of the reaction is preferably in the range of 5 minutes to 50 hours, more preferably 30 minutes to 30 hours and most preferably 1 hour to 10 hours.

In continuous processes, the residence time is preferably 5 minutes to 50 hours, more preferably 30 minutes to 30 hours and most preferably 1 hour to 10 hours.

The tetramethylglycolide prepared can be used immediately for some applications, without further purification steps. In addition, the tetramethyl-glycolide can additionally be purified by distillation or chromatographic processes. For this purpose, it is possible in particular to use prior art processes, as described, for example, in EP-A-0 834 511.

In addition, the tetramethylglycolide prepared can also be removed by extraction from the reaction mixture, for which suitable extractants are known per se. These media should have a low miscibility with the starting materials, although a high proportion of the product should be transferred into the extractant.

In a particular aspect, the process according to the invention can be performed in combination with a process for preparing alkyl methacrylates. The process according to the invention can therefore serve very flexibly for the preparation of several commercially significant products, while allowing high utilization of the plants to be achieved.

A particularly preferred process may, for example, comprise the following steps:
A) formation of acetone cyanohydrin by reacting acetone with hydrocyanic acid;
B) hydrolysis of the acetone cyanohydrin to form 2-hydroxyisobutyramide;
C) alcoholysis of the 2-hydroxyisobutyramide to obtain a 2-hydroxyisobutyric ester;
D) transesterification of the 2-hydroxyisobutyric ester or of the 2-hydroxyisobutyric esters with methacrylic acid to form at least one alkyl methacrylate and 2-hydroxyisobutyric acid;
E) dehydration of the 2-hydroxyisobutyric acid to form methacrylic acid.

In this process, tetramethylglycolide is prepared in accordance with the invention from a portion of the 2-hydroxyisobutyric acid obtained in step D). The content of tetramethylglycolide and the content of alkyl methacrylate can be controlled, for example, via the reaction temperature and the pressure, and also the water content of the reaction. The higher the water content in the transesterification, the more alcohol can be released in the transesterification, so that a portion of the 2-hydroxyisobutyric ester is converted by hydrolysis to 2-hydroxyisobutyric acid from which tetramethylglycolide can subsequently be formed. In addition, the proportion of 2-hydroxyisobutyric acid can be controlled via the temperature. The amount of tetramethylglycolide which is formed from the 2-hydroxyisobutyric acid prepared in step D) can be controlled in particular via the temperature and the residence time.

In a first step, acetone is reacted with hydrocyanic acid to give the corresponding acetone cyanohydrin. This reaction is effected generally using a small amount of alkali or of an amine as a catalyst.

In a further step, the acetone cyanohydrin thus obtained is reacted with water to give 2-hydroxy-isobutyramide.

Typically, this reaction is performed in the presence of a catalyst. Suitable catalysts for this purpose are in particular manganese oxide catalysts, as described, for example, in EP-A-0945429, EP-A-0561614 and EP-A-0545697. In this case, the manganese oxide can be used in the form of manganese dioxide, which is obtained by treating manganese sulphate with potassium permanganate under acidic conditions (cf. Biochem. J., 50 p. 43 (1951) and J. Chem. Soc., p. 2189, 1953) or by electrolytic oxidation of manganese sulphate in aqueous solution. In general, the catalyst is in many cases used in the form of powder or granule with a suitable particle size. In addition, the catalyst can be applied to a support. In this case, it is possible in particular also to use so-called slurry reactors or fixed bed reactors, which are described, inter alia, in EP-A-956 898.

In addition, the hydrolysis reaction can be catalysed by enzymes. The suitable enzymes include nitrile hydratases. This reaction is described by way of example in "Screening, Characterization and Application of Cyanide-resistant Nitrile Hydratases" Eng. Life Sci. 2004, 4, No. 6.

Furthermore, the hydrolysis reaction can be catalysed by acids, especially sulphuric acid. This is detailed, inter alia, in JP Hei 4-193845.

The water which is needed to hydrolyse the acetone cyanohydrin can in many cases be used as the solvent. The molar ratio of water to cyanohydrin is preferably at least 1; the molar ratio of water to cyanohydrin is more preferably in the range of 0.5:1-25:1 and most preferably in the range of 1:1-10:1.

The water used for the hydrolysis may have a high purity. However, this property is not obligatory. Thus, in addition to fresh water, it is also possible to use service water or process water which comprises greater or lesser amounts of impurities. Accordingly, it is also possible to use recycled water for the hydrolysis.

In addition, further constituents may be present in the reaction mixture for the hydrolysis of the cyanohydrin. These include aldehydes and ketones, especially acetone which has been used to prepare the acetone cyanohydrin. This is described, for example, in U.S. Pat. No. 4,018,829-A. The purity of the aldehydes and/or ketones added is generally not particularly critical. Accordingly, these substances may contain impurities, especially alcohols, for example methanol, water and/or methyl 2-hydroxy-isobutyrate (MHIB). The amount of carbonyl compounds, especially acetone and/or acetaldehyde, in the reaction mixture may be adjusted within wide ranges. Preference is given to using the carbonyl compound in an amount in the range of 0.1-6 mol, preferably 0.1-2 mol, per mole of cyanohydrin.

The temperature at which the hydrolysis reaction is effected may generally be within the range of 10-150° C., preferably within the range of 20-100° C. and more preferably within the range of 30-80° C.

The reaction can be performed, for example, in a fixed bed reactor or in a suspension reactor.

The reaction mixture thus obtained comprises generally, in addition to the desired 2-hydroxyisobutyramide, further constituents, especially unconverted acetone cyanohydrin, and also any acetone and/or acetaldehyde used. Accordingly, the reaction mixture can be purified, which can cleave unconverted acetone cyanohydrin to acetone and hydrocyanic acid, in order to use them again to prepare the cyanohydrin. The same applies to the acetone and/or acetaldehyde removed.

In addition, the purified reaction mixture comprising hydroxy amide can be purified to remove further constituents by means of ion exchange columns.

For this purpose, it is possible in particular to use cation exchangers and anion exchangers. Ion exchangers suitable for this purpose are known per se. For example, suitable cation exchangers can be obtained by sulphonating styrene-divinylbenzene copolymers. Basic anion exchangers include quaternary ammonium groups which are bonded covalently to styrene-divinylbenzene copolymers.

The steps for the preparation of α-hydroxycarboxamides are described in detail, inter alia, in EP-A-0686623.

In the next step C), the 2-hydroxyisobutyramide thus obtained can be converted to the alkyl 2-hydroxy-carboxylate. This can be effected, for example, by the use of alkyl formates. Methyl formate or a mixture of methanol and carbon monoxide are especially suitable, this reaction being described by way of example in EP-A-0407811.

Preference is given to reacting the 2-hydroxy-isobutyramide by alcoholysis with an alcohol which preferably comprises 1-10 carbon atoms, more preferably 1-5 carbon atoms. Preferred alcohols include methanol, ethanol, propanol, butanol, especially n-butanol and 2-methyl-1-propanol, pentanol, hexanol, heptanol, 2-ethylhexanol, octanol, nonanol and decanol. The alcohol used is more preferably methanol and/or ethanol, very particular preference being given to methanol. The reaction with carboxamides with alcohols to obtain carboxylic esters is common knowledge.

This reaction can be accelerated, for example, by basic catalysts. These include homogeneous catalysts and heterogeneous catalysts.

The homogeneous catalysts include alkali metal alkoxides and organometallic compounds of titanium, tin and aluminium. Preference is given to using a titanium alkoxide or tin alkoxide, for example titanium tetraisopropoxide or tin tetrabutoxide. The heterogeneous catalysts include magnesium oxide, calcium oxide and basic ion exchangers as have been described above.

The molar ratio of 2-hydroxyisobutyramide to alcohol, for example methanol, is not critical per se, and is preferably in the range of 2:1-1:20.

The reaction temperature may likewise be within wide limits, the reaction rate generally increasing with increasing temperature. The upper temperature limit arises generally from the boiling point of the alcohol used. The reaction temperature is preferably in the range of 40-300° C., more preferably 160-240° C. Depending on the reaction temperature, the reaction may be performed at reduced or elevated pressure. Preference is given to performing this reaction in a pressure range of 0.5-35 bar, more preferably 5 to 30 bar.

Typically, the ammonia formed is discharged from the reaction system, the reaction being performed in many cases at the boiling point.

The ammonia released in the alcoholysis can be returned to the overall process easily. For example, ammonia can be reacted with methanol to give hydrocyanic acid. This is detailed, for example, in EP-A-0941984. In addition, the hydrocyanic acid can be obtained from ammonia and methane by the BMA or Andrussow process, these processes being described in Ullmann's Encyclopedia of Industrial Chemistry, 5th edition on CD-ROM, under "Inorganic Cyano Compounds".

In a next step D), the 2-hydroxyisobutyric ester is reacted with methacrylic acid (2-methylpropenoic acid) to obtain alkyl methacrylate and 2-hydroxyisobutyric acid.

In a further aspect of the present invention, 2-hydroxyisobutyric esters can be reacted with methacrylic acid. The 2-hydroxyisobutyric esters used for this purpose are known per se, the alcohol radical of the ester comprising preferably 1 to 20 carbon atoms, in particular 1 to 10 carbon atoms and more preferably 1 to 5 carbon atoms. Preferred alcohol radicals derive in particular from methanol, ethanol, propanol, butanol, especially n-butanol and 2-methyl-1-propanol, pentanol, hexanol and 2-ethylhexanol, particular preference being given to methanol and ethanol.

2-Hydroxyisobutyric esters used with preference are methyl α-hydroxyisobutyrate and ethyl α-hydroxy-isobutyrate.

In addition to the reactants, the reaction mixture may comprise further constituents, for example solvents, catalysts, polymerization inhibitors and water.

The reaction of the 2-hydroxyisobutyric ester with methacrylic acid can be catalysed by at least one acid or at least one base. In this case, it is possible to use either homogeneous or heterogeneous catalysts. Preferred acidic catalysts have been detailed above, and cation exchange resins in particular, such as sulphonic acid-containing styrene-divinylbenzene polymers, are particularly suitable.

The particularly suitable cation exchange resins include in particular sulphonic acid-containing styrene-divinylbenzene polymers. Particularly suitable cation exchange resins can be obtained commercially from Rohm&Haas under the trade name Amberlyst® and from Lanxess under the trade name Lewatit®.

The concentration of catalyst is preferably in the range of 1 to 30% by weight, more preferably 5 to 15% by weight, based on the sum of the 2-hydroxyisobutyric ester used and of the methacrylic acid used.

The polymerization inhibitors usable with preference include phenothiazine, tert-butylcatechol, hydroquinone monomethyl ether, hydroquinone, 4-hydroxy-2,2,6,6-tetramethylpiperidinooxyl (TEMPOL) or mixtures thereof; the effectiveness of these inhibitors can be improved in some cases by use of oxygen. The polymerization inhibitors can be used in a concentration in the range of 0.001 to 2.0% by weight, more preferably in the range of 0.01 to 0.2% by weight, based on the sum of the 2-hydroxyisobutyric ester used and of the methacrylic acid used.

The reaction is performed preferably at temperatures in the range of 50° C. to 200° C., more preferably 70° C. to 130° C., in particular 80° C. to 120° C. and most preferably 90° C. to 110° C.

The reaction can be performed at reduced or elevated pressure depending on the reaction temperature. This reaction is performed preferably at a pressure in the range of 0.02-5 bar, in particular 0.2 to 3 bar and more preferably 0.3 to 0.5 bar.

The molar ratio of methacrylic acid to the 2-hydroxyisobutyric ester is preferably in the range of 4:1-1:4, especially 3:1 to 1:3 and more preferably in the range of 2:1-1:2.

The selectivity is preferably at least 90%, more preferably 98%. The selectivity is defined as the ratio of the sum of amounts of alkyl methacrylates and 2-hydroxyisobutyric acid formed, based on the sum of the amounts of 2-hydroxyisobutyric ester and methacrylic acid converted.

In a particular aspect of the present invention, the transesterification can be effected in the presence of water. The water content is preferably in the range of 0.1-50% by weight, more preferably 0.5-20% by weight and most preferably 1-10% by weight, based on the weight of the 2-hydroxyisobutyric ester used.

The addition of small amounts of water surprisingly allows the selectivity of the reaction to be increased. In spite of water addition, the formation of methanol can be kept surprisingly low. At a water concentration of 10 to 15% by weight, based on the weight of the 2-hydroxyisobutyric ester used, preferably less than 5% by weight of methanol forms at a reaction temperature of 120° C. and a reaction time or residence time of 5 to 180 min.

The transesterification can be performed batchwise or continuously, preference being given to continuous processes.

The reaction time of the transesterification depends upon the molar masses and the reaction temperature used, these parameters being within wide ranges. The reaction time of the transesterification of the 2-hydroxyisobutyric ester with methacrylic acid is preferably in the range of 30 seconds to 15 hours, more preferably 5 minutes to 5 hours and most preferably 15 minutes to 3 hours.

In continuous processes, the residence time is preferably 30 seconds to 15 hours, more preferably 5 minutes to 5 hours and most preferably 15 minutes to 3 hours.

In the preparation of methyl methacrylate from methyl α-hydroxyisobutyrate, the temperature is preferably 60 to 130° C., more preferably 80 to 120° C. and most preferably 90 to 110° C. The pressure is preferably in the range of 50 to 1000 mbar, more preferably 300 to 800 mbar. The molar ratio of methacrylic acid to methyl α-hydroxyisobutyrate is preferably in the range of 2:1-1:2, in particular 1.5:1-1:1.5.

In a particularly preferred embodiment, the transesterification can be effected in a still. In this case, the catalyst can be added in any region of the still. For example, the catalyst can be provided in the region of the bottom or in the region of the column. At the same time, however, the reactants should be brought into contact with the catalyst. In addition, catalysts may be provided in a separate region of the still, in which case this region is connected to the further regions of the still, for example the bottom and/or the column. This separate arrangement of the catalyst region is preferred.

This preferred embodiment surprisingly succeeds in increasing the selectivity of the reaction. In this context, it should be emphasized that the pressure of the reaction can be adjusted independently of the pressure within the distillation columns. This allows the boiling temperature to be kept low without the reaction time or the residence time rising correspondingly. In addition, the temperature of the reaction can be varied over a wide range. This allows the reaction time to be shortened. In addition, the volume of catalyst can be selected as desired without needing to take account of the geometry of the column. Furthermore, for example, a further reactant can be added. All of these measures can contribute to the increase in the selectivity and the productivity, surprising synergistic effects being achieved.

In this process, methyl 2-hydroxyisobutyrate is fed to the still. In addition, methacrylic acid is introduced into the still. The distillation conditions are preferably configured in such a way that exactly one product is discharged from the still by distillation, the second product remaining in the bottom and being removed continuously therefrom. In the case of use of alcohols with a low carbon number, especially ethanol or methanol, preference is given to withdrawing the alkyl methacrylate from the reaction mixture by distillation. The reactants are passed cyclically through the catalyst region. This continuously forms alkyl methacrylate and 2-hydroxyisobutyric acid.

A preferred embodiment of a still is shown schematically in FIG. 1. The reactants may be introduced into the distillation column (3) via one common line (1) or separately via two lines (1) and (2). The reactants are preferably added via separate lines. The reactants can be fed to the column at the same stage or in any position.

The temperature of the reactants can be adjusted by means of a heat exchanger in the feed, the units needed for this purpose not being shown in FIG. 1. In a preferred variant, the reactants are metered separately into the column, the lower-boiling component being metered in below the position for the feeding of the higher-boiling compound. In this case, the lower-boiling component is preferably added in vaporous form.

For the present invention, any multistage distillation column (3) which has two or more separating stages may be used. The number of separating stages used in the present invention is the number of trays in a tray column or the number of theoretical plates in the case of a column with structured packing or a column with random packings.

Examples of a multistage distillation column with trays include those such as bubble-cap trays, sieve trays, tunnel-cap trays, valve trays, slot trays, slotted sieve trays, bubble-cap sieve trays, jet trays, centrifugal trays; for a multistage distillation column with random packings, those such as Raschig rings, Lessing rings, Pall rings, Berl saddles, Intalox saddles; and, for a multistage distillation column with structured packings, those such as Mellapak (Sulzer), Rombopak (Kühni), Montz-Pak (Montz) and structured packings with catalyst pockets, for example Kata-Pak.

A distillation column with combinations of regions of trays, of regions of random packings or of regions of structured packings may likewise be used.

The column (3) may be equipped with internals. The column preferably has a condenser (12) for condensing the vapour and a bottom evaporator (18).

The distillation apparatus preferably has at least one region, referred to hereinafter as reactor, in which at least one catalyst is provided. This reactor may be within the distillation column. However, this reactor is preferably arranged outside the column (3) in a separate region, one of these preferred embodiments being explained in detail in FIG. 1.

In order to carry out the transesterification reaction in a separate reactor (8), it is possible within the column to collect a portion of the liquid phase flowing downwards by means of a collector and to pass it out of the column as a substream (4). The position of the collector is determined by the concentration profile in the column of the individual components. The concentration profile can be regulated by means of the temperature and/or the reflux. The collector is preferably positioned such that the stream conducted out of the column contains both reactants, more preferably the reactants in sufficiently high concentration and most preferably in a molar acid:ester ratio=1.5:1 to 1:1.5. In addition, a plurality of collectors may be provided at various points in the distillation column, in which case the amount of reactants withdrawn can be used to adjust the molar ratios.

It is additionally possible for a further reactant, for example water, to be metered into the stream conducted out of the column, in order to adjust the acid/ester product ratio in the cross-transesterification reaction or to increase the selectivity. The water can be fed from outside via a line (not shown in FIG. 1) or withdrawn from a phase separator (13). The pressure of the stream (5) enriched with water can then be increased by a means for pressure increase (6), for example a pump.

An increase in the pressure can reduce or prevent formation of steam in the reactor, for example a fixed bed reactor. This allows uniform flow through the reactor and wetting of the catalyst particles. The stream can be conducted through a heat exchanger (7) and the reaction temperature adjusted. The stream can be heated or cooled as required. It is additionally possible to adjust the ester to acid product ratio via the reaction temperature.

The transesterification reaction takes place over the catalyst in the fixed bed reactor (8). The flow through the reactor may be downwards or upwards. The reactor output stream (9) comprising the products and the unconverted reactants to a certain degree, the content of the components in the reactor waste stream depending upon the residence time, the catalyst mass, the reaction temperature and the reactant ratio and the amount of water added, is first passed through a heat exchanger (10) and adjusted to a temperature which is advantageous for the introduction into the distillation column. Preference is given to setting the temperature which corresponds to the temperature in the distillation column at the point of introduction of the stream.

The position where the stream leaving the reactor is returned into the column may lie above or below the position for the withdrawal of the reactor feed, but will preferably be above it. Before the recycling into the column, the stream may be decompressed through a valve (11), which preferably establishes the same pressure level as in the column. In this context, the distillation column preferably has a lower pressure. This configuration offers the advantage that the boiling points of the components to be separated are lower, as a result of which the distillation can be carried out at a lower temperature level, as a result of which it saves energy and is more thermally gentle.

In the distillation column (3), the product mixture is then separated. The low boiler, preferably the ester formed in the transesterification, is removed via the top. The distillation column is preferably operated such that the water added upstream of the fixed bed reactor is likewise removed as the top product. The vaporous stream drawn off at the top is condensed in a condenser (12) and then separated in a decanter (13) into the aqueous phase and product ester-containing phase. The aqueous phase can be discharged to the workup via the line (15) or returned fully or partly back into the reaction via line (17). The stream of the ester-containing phase can be conducted via line (14) partly as reflux (16) to the column or discharged partly from the still. The high boiler, preferably the acid formed in the cross-transesterification, is discharged from the column (19) as a bottom stream.

Figure 2:
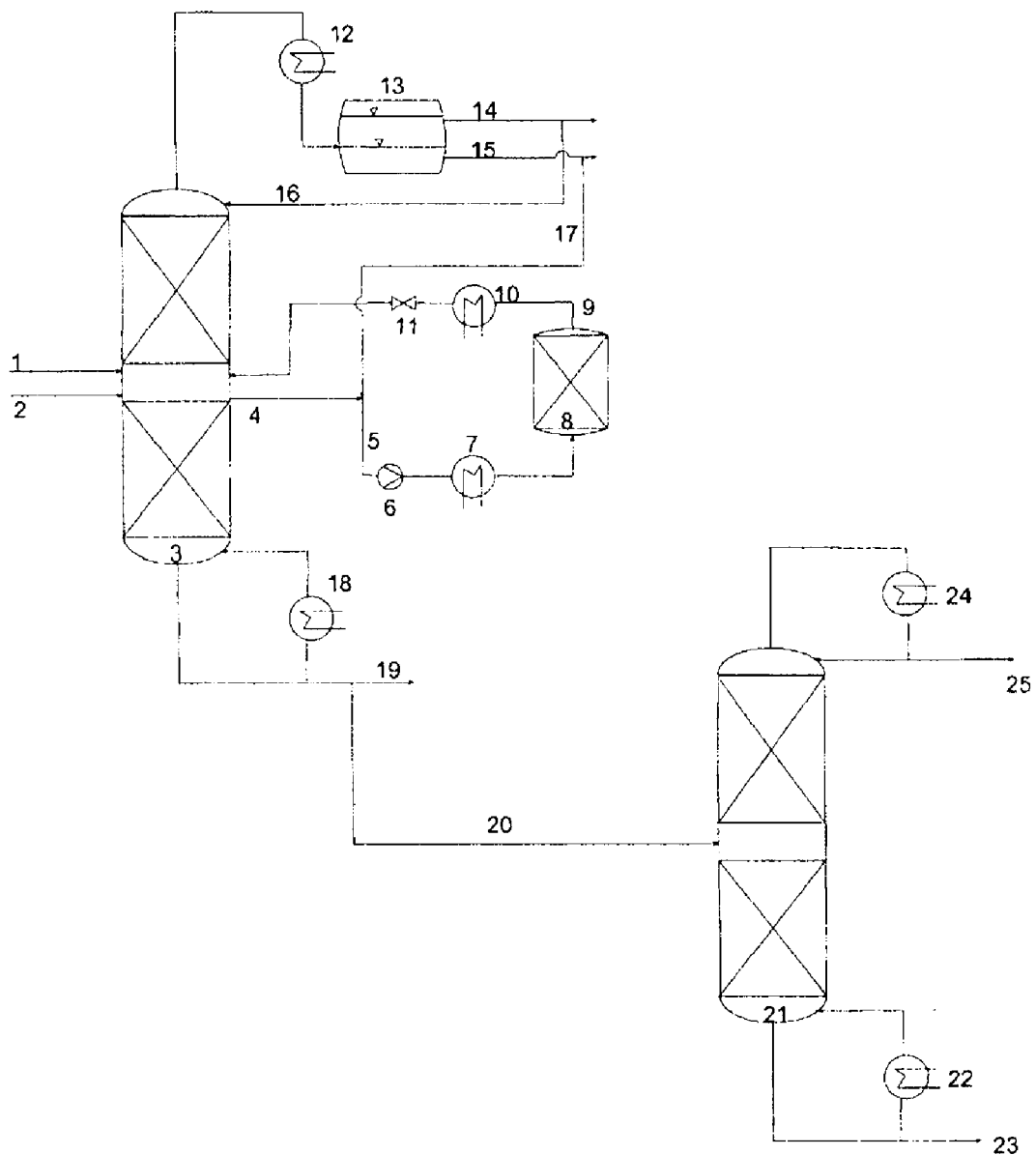
FIG. 2 is a schematic of one embodiment of a reactive still that is described herein.

A further embodiment of a particular reactive still is shown in FIG. 2, which is substantially similar to the embodiment detailed above, so that merely the differences are addressed below, the same reference numerals being used for the same parts and the above description applying correspondingly.

The reactive still shown in FIG. 2 has a second distillation column (21) which is connected via line (20) to the above-described line (19) or to the bottom of the distillation column (3). Depending on the residence time in the bottom of the distillation column (3), the composition withdrawn may contain greater or lesser amounts of 2-hydroxyisobutyric acid. In the bottom of the distillation column (21) equipped with a bottom evaporator (22), the 2-hydroxyisobutyric acid can be converted to tetramethylglycolide and be withdrawn from the plant via line 23. In distillation column (21), water can be removed from the composition, condensed with a condenser (24) and withdrawn from the still.

If the 2-hydroxyisobutyric acid present in the bottoms of the distillation column (3) has been converted to tetramethylglycolide in a high amount, this plant likewise enables purification of the resulting tetramethylglycolide. In this case, tetramethyl-glycolide can be withdrawn via the top. The stream withdrawn from the bottom comprises a high proportion of 2-hydroxyisobutyric acid in relation to the added stream.

The 2-hydroxyisobutyric acid obtained from the reaction can be dehydrated in a known manner in a further step E). In general, the α-hydroxyisobutyric acid is heated in the presence of at least one metal salt, for example of alkali metal and/or alkaline earth metal salts, to temperatures in the range of 160-300° C., more preferably in the range of 200 to 240° C., to generally obtain methacrylic acid and water. The suitable metal salts include sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate and sodium dihydrogenphosphate.

The dehydration of the α-hydroxycarboxylic acid can be performed preferably at a pressure in the range of 0.05 bar to 2.5 bar, more preferably in the range of 0.1 bar to 1 bar.

The dehydration of α-hydroxycarboxylic acids is described, for example, in DE-A-176 82 53.

The methacrylic acid thus obtained can be used in turn to prepare alkyl methacrylates. In addition, methacrylic acid is a commercial product. Surprisingly, the process for preparing alkyl methacrylates can accordingly likewise serve to prepare methacrylic acid, in which case the product ratio of alkyl (meth)acrylates to methacrylic acid can be regulated easily by the concentration of water in the transesterification of the alkyl α-hydroxycarboxylate and/or by the reaction temperature.

The present invention will be illustrated in detail hereinafter with reference to examples.

EXAMPLE 1

1.2 kg (11.54 mol) of pure 2-hydroxyisobutyric acid (HIBA) were introduced into a still with column and condenser. The pressure was adjusted to 400 mbar and the reaction temperature was adjusted to approx. 180° C., the bottom temperatures being specified in Table 1. Water was removed from the reaction mixture continuously by distillation. The temperature at the top of the still was approx. 76° C. After the time intervals shown in Table 1, samples were taken from the bottoms and analysed by means of gas chromatography.

TABLE 1

| Time [min] | Temperature of the bottoms [° C.] | Tetramethyl-glycolide [% by wt.] | HIBA [% by wt.] |
|---|---|---|---|
| 79 | 178 | 40.19 | 58.07 |
| 139 | 180 | 56.04 | 42.95 |

TABLE 1-continued

| Time [min] | Temperature of the bottoms [° C.] | Tetramethyl-glycolide [% by wt.] | HIBA [% by wt.] |
|---|---|---|---|
| 199 | 184 | 74.48 | 23.72 |
| 259 | 185 | 80.84 | 18.25 |
| 334 | 188 | 95.20 | 2.63 |
| 414 | 187 | 95.45 | 2.70 |
| 504 | 188 | 97.60 | 0.23 |
| 594 | 182 | 98.19 | 0.24 |
| 604 | 182 | 98.27 | 0.23 |

It has been shown that, surprisingly, when 2-hydroxyisobutyric acid is used as the reactant, essentially pure tetramethylglycolide is formed as the cyclic ester.

The invention claimed is:

1. A process for preparing tetramethylglycolide, comprising heating a composition to a temperature of at least 100° C. thereby producing the tetramethylglycolide, wherein the composition consists essentially of 2-hydroxy-isobutyric acid, optionally water, and optionally tetramethylglycolide.

2. The process according to claim 1, wherein the composition consists essentially of at least 70% by weight of at least one of 2-hydroxyisobutyric acid and tetramethylglycolide.

3. The process according to claim 1 wherein the reaction is performed in a still.

4. The process according to claim 3, wherein water formed is removed from the reaction mixture by distillation.

5. The process according to claim 1, wherein the reaction is effected at a temperature of at least 150° C.

6. The process according to claim 1, wherein the reaction is performed continuously.

7. The process according to claim 1, wherein the reaction is performed at a pressure of 0.1 to 0.4 bar.

8. The process according to claim 1, wherein the reaction is effected autocatalytically.

9. The process according to claim 1, wherein the resulting tetramethylglycolide is purified by distillation.

10. The process according to claim 1, wherein the resulting tetramethylglycolide is purified by extraction.

11. The process according to claim 1, wherein the process is performed in combination with a process for preparing alkyl methacrylates.

12. The process according to claim 11, comprising:
(A) formation of acetone cyanohydrin by reacting acetone with hydrocyanic acid;
(B) hydrolysis of the acetone cyanohydrin to form 2-hydroxyisobutyramide;
(C) alcoholysis of the 2-hydroxyisobutyramide to obtain a 2-hydroxyisobutyric ester;
(D) transesterification of the 2-hydroxyisobutyric ester or of the 2-hydroxyisobutyric esters with methacrylic acid to form at least one alkyl methacrylate and 2-hydroxyisobutyric acid;
(E) dehydration of the 2-hydroxyisobutyric acid to form methacrylic acid.

13. The process according to claim 12, wherein the transesterification of the alkyl α-hydroxycarboxylate with methacrylic acid is catalysed by an acid.

14. The process according to claim 13, wherein the acid is an ion exchanger.

15. The process according to claim 12, wherein the transesterification is performed in a still.

16. The process according to claim 12, wherein the transesterification of the α-hydroxyisobutyric ester with methacrylic acid is performed at a pressure in the range of 100 mbar to 3 bar.

17. The process according to claim 12, wherein the transesterification of the α-hydroxyisobutyrate with methacrylic acid is performed at a temperature in the range of 70 to 130° C.

18. The process according to claim 12, wherein the transesterification of the 2-hydroxyisobutyric ester with methacrylic acid is performed in the presence of water.

19. The process according to claim 11, wherein methyl methacrylate is prepared.

20. The process according to claim 12, wherein methyl methacrylate is prepared.

21. The process according to claim 1, wherein the composition consists of water and 2-hydroxy-isobutyric acid.

22. The process according to claim 1, wherein the composition consists of 2-hydroxy-isobutyric acid.

23. The process according to claim 1, wherein the composition consists of water, 2-hydroxy-isobutyric acid, and tetramethylglycolide.

24. The process according to claim 1, which is conducted in a still, at a pressure of from 0.01 to 0.4 bar, and a temperature of at least 170° C.

* * * * *